United States Patent [19]

Kanamaru et al.

[11] Patent Number: 5,135,920
[45] Date of Patent: Aug. 4, 1992

[54] ANGIOSTATIC AGENTS

[75] Inventors: Tsuneo Kanamaru, Takatsuki; Yukimasa Nozaki, Ikeda; Katsuichi Sudo, Takatsuki, all of Japan

[73] Assignee: Takeda Chemical Industries, Ltd., Osaka, Japan

[21] Appl. No.: 434,440

[22] Filed: Nov. 9, 1989

[30] Foreign Application Priority Data

Nov. 16, 1988 [JP] Japan .................. 63-289782

[51] Int. Cl.$^5$ ...................... A61K 9/06; A61K 31/715
[52] U.S. Cl. ..................................... 514/59; 514/824; 514/863; 514/866; 536/1.1; 536/112; 536/118; 536/122
[58] Field of Search ................. 514/59, 824, 863, 866; 536/112, 1.1, 118, 122

[56] References Cited

U.S. PATENT DOCUMENTS

| | | | |
|---|---|---|---|
| 3,754,925 | 8/1973 | Kimura et al. | 536/1.1 |
| 4,207,312 | 6/1980 | Fujii et al. | 514/59 |
| 4,767,614 | 8/1988 | Scarpa et al. | 514/59 |
| 4,793,336 | 12/1988 | Wang | 514/59 |
| 4,820,693 | 4/1989 | Gillespie | 514/25 |
| 4,833,131 | 5/1989 | Williams et al. | 514/54 |
| 4,840,941 | 6/1989 | Ueno et al. | 514/59 |
| 4,876,250 | 10/1989 | Clark | 514/179 |
| 4,895,838 | 1/1990 | McCluer et al. | 514/53 |
| 4,912,093 | 3/1990 | Michaeli | 514/53 |
| 4,921,838 | 5/1990 | Catsimpoolas et al. | 514/53 |
| 4,965,347 | 10/1990 | Misaki et al. | 514/54 |
| 4,966,890 | 10/1990 | Gillespie | 514/25 |
| 5,055,301 | 10/1991 | Voigt et al. | 514/59 |

FOREIGN PATENT DOCUMENTS

| | | |
|---|---|---|
| 325199 | 7/1989 | European Pat. Off. . |
| 43-7000 | 3/1968 | Japan . |
| 5083798 | 6/1980 | Japan . |

OTHER PUBLICATIONS

Ingber et al., "A Possible Mechanism for Inhibition of Angiogenesis by Angiostatic Steroids:Induction of Capillary Basement Membrane Dissolution"; *Endocrinology*, vol. 119, No. 4, Oct. 1986, pp. 1768-1775.
Taylor et al., "Protamine is an inhibitor of angiogenesis"; *Nature*, vol. 297, May 27, 1982, pp. 307-312.
Advances in Cancer Research, 43, 175 (1985).
Science, 221, 719 (1983).
Annals of Surgery, 206, 374 (1987).
Laboratory investigation, 59, 44 (1988).
J. Pharmacol. Exp. Ther., 244, 729 (1988).
The Merck Index, 9th edition, 1976, Paragraph 2907, p. 387.
The Merck Index, 11th edition, 1989, Paragraph 2925, pp. 464-465 and Paragraph 4571, p. 735.
Carbohydrate Res., 17, 109 (1971).
J. Biol. Chem., 239, 2986 (1964).
J. Antibiotics, 34, 1355 (1981).
Biochem. Pharmacology, 31, 915 (1982).
J. Antibiotics, 40, 1231 (1987).
J. Antiboitcs, 40, 1239 (1987).
J. Am. Chem. Soc., 83, 3096 (1961).
Science, 230, 1375 (1985).
Endocr. 1768-1775 (1986), vol. 119, Ingber, et al.

*Primary Examiner*—Ronald W. Griffin
*Attorney, Agent, or Firm*—David G. Conlin; Gregory D. Williams; David S. Resnick

[57] ABSTRACT

Dextran sulfate, $\beta$-1,3-glucan sulfate, and the salts thereof are angiostatic and useful for treatment and prevention of various diseases caused by abnormally accelerated angiogenesis. Combination of such a compound with a steroidal or non-steroidal substance increases the angiostatic activity of each compound to induce the combined effect.

8 Claims, No Drawings

ANGIOSTATIC AGENTS

This invention relates to angiostatic agents.

Angiogenesis is known to occur not only in normal physiological events in human and animals such as embryogenesis or ovulation or placentation in the female sexual cycle, but also in repair processes such as wound healing and inflammation and in various pathological events where rapidly grown and proliferated capillaries damage tissues seriously. Diseases due to such pathological growth of capillaries include diabetic retinopathy, retrolenticular fibroplasia, angiogenesis following keratoplasty, glaucoma, ocular tumor and trachoma in ophthalmology, psoriasis and purulent granuloma in dermatology, hemangioma and fibrous hemangioma in pediatrics, hypertrophic scar and granulation in surgery, rheumatic arthritis and edematous sclerosis in internal medicine, and arteriosclerosis and various tumors among heart diseases.

In particular, abnormally increased angiogenesis in diabetic retinopathy and trachoma causes loss of eye sight in many people, and abnormal angiogensis in the joints may break cartilage in the joints, inflicting rheumatic arthritis on many patients. Thus development of substances has been desired which are useful for treatment and prevention of such diseases accompanying abnormally increased angiogenesis.

Rapid growth of tumors is believed to be a result of angiogenesis induced by angiogenetic factor produced by tumor cells. Because angiostatic agents are expected to be new therapeutic agents against various tumors, studies exploring such agents have begun [J. Folkman; Advances in cancer Research, 43 175, 1985, edited by George Klein and Sidney Weinhouse].

It has already been reported that heparin or a heparin fragment combined with a so-called angiostatic steroid such as cortisone inhibits angiogenesis (J. Folkman et al.; Science, 221 719 (1983), J. Folkman et al.; Annals of Surgery, 206 374 (1987)).

It has also been found that an α-, β- or γ-cyclodextrin sulfate, particularly β-cyclodextrin tetradecasulfate, or heparin, in combination with an angiostatic steroid described above, fumagillin, or a collagen synthesis inhibitor exerts a synergistic angiostatic effect (D. Ingber and J. Folkman; Laboratory Investigation, 59, 44 (1988)).

Basement membrane and collagen synthesis in the membrane have been pointed out to play an important role in angiogenesis (M. E. Maragoudakis, M. Sarmonika and M. Panoutsacopoulous; J. Pharmacol. Exp. Ther. 244, 729 (1988), D. E. Ingber, J. A. Madri and J. Folkman; Endocrinology, 119, 1768 (1986)).

Under these circumstances investigators including the inventors have continued the studies exploring angiostatic agents, and found that fumagillin produced by *Aspergillus fumigatus* known hitherto as an antibiotic and antiprotozoal agent exerts strong angiostatic effect which is potentiated by combination with heparin or β-cyclodextrin tetradecasulfate [J. Folkman and T. Kanamura et al.; EP Publication (laid open) No. EP-A-325199.

In accordance with the present invention, the inventors have found that dextran sulfate, β-1,3-glucan sulfate and the salts thereof show angiostatic activity, have few side effects and are available at low cost. It has also been found that the angiostatic effect is potentiated when dextran sulfate, β-1,3-glucan sulfate, or a salt thereof is combined with a steroid or a non-steroidal compound which inhibits angiogenesis by itself or potentiates the inhibition.

This invention relates to (1) Angiostatic agents containing dextran sulfate, β-1,3-glucan sulfate, or a pharmaceutically acceptable salt thereof, (2) angiostatic agents prepared by combination of (a) dextran sulfate, β-1,3-glucan sulfate, or a pharmaceutically acceptable salt thereof, with (b) a steroidal or non-steroidal substance which accelerates the angiostatic effect.

In the present invention, dextran sulfate and the salts thereof prepared by the method, for example, shown as Reference Example 1 below. The starting material dextran is composed mainly of an α-1,6-linked D-glucose polymer produced by bacteria such as *Leuconostoc mesenteroides* and *Leuconostoc dextranicum* and, has long been used clinically as a substitute for blood plasma (The Merck Index, 9th edition, 1976, Paragraph 2907, p386-387; Seikagaku Jiten, Tokyo Kagaku Dojin, 1984, p.877).

Dextran sulfate used in this invention is desirably of a molecular weight in the range of about 5,000 to 500,000 and the degree of sulfation expressed in terms of sulfur (S) content is of about 16 to 18 weight %. The pharmaceutically acceptable salts thereof include ammonium salts, alkali metal salts (e.g. sodium salts, potassium salts) and alkali earth metal salts (e.g. calcium salts, magnesium salts).

β-1,3-glucan sulfate used in the invention means the sulfate of the straight chain β-1,3-glucan represented by the formula (I):

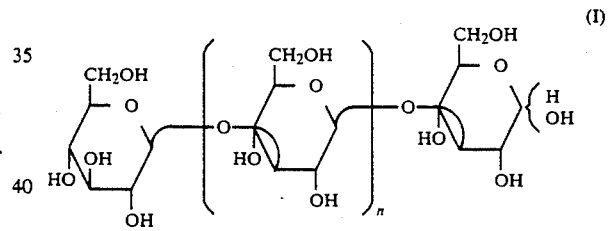

wherein n is an integer from 4 to about 1000, and appropriate numbers of three hydroxyl groups of the intermediate monosaccharide units and the hydroxyl groups of the terminal monosaccharide units are sulfonated.

In this invention, the mean degree of substitution ($\overline{DS}$) with a sulfonic acid group in a monosaccharide unit is usually 0.5 to 3, and per monosaccharide of $\overline{DS}$ of 1 to 2 are advantageously used. The degree of substitution corresponds to about 10 to 20 weight % sulfur content.

The β-1,3-glucans described above may be any of those with mean degree of polymerization ($\overline{DP}$) of less than 1,000, desirably about 40 to 600. Such β-1,3-glucans are exemplified by curdlan (known also as "heat coagulating polysaccharide PS") which is known as a water-insoluble, heat-coagulating glucan composed mainly of a straight chain β-1,3-linked glucose units, produced by microorganisms belonging to Alcaligenes or Agrobacterium (Japanese Patent Publication No. 7000/68, No. 32673/73, No. 32674/73). The properties and the method for production of partial hydrolyzate preparations of curdlan are described in detail in Japanese Patent Publication Laid Open No. 83798/1980. Such a partial hydrolyzate preparation is of $\overline{DP}$ of 30 to about 800, desirably 40 to about 600.

In the formula (I), relation between n and $\overline{DP}$ is expressed as $\overline{DP} - 2 = n$.

Hydrolysis is performed with a conventional method, such as acid hydrolysis, alkali hydrolysis, or an enzymic method using β-1,3-glucanase.

Separation of β-1,3-glucan low polymers from the reaction mixture is performed by various methods used for purification and fractionation of polysaccharides and oligosaccharides, such as precipitation at an acidic pH, precipitation by addition of ethanol, and gel filtration. By such a method, various low polymers with a desirable mean degree of polymerization can be separated. Mean degree of polymerization of β-1,3-glucan and of the low polymers can be determined by the method of Manners et al. (Carbohydrate Res., 17, 109 (1971)).

Method for preparation of sulfuric acid esters of β-1,3-glucan represented by the formula (I) is described in the following.

β-1,3-glucan and the low polymers thereof can be sulfated with a sulfating agent such as chlorosulfonic acid or anhydrous sulfuric acid in the presence of pyridine, formamide or dimethylformamide, or with a composite of anhydrous sulfuric acid with an organic base such as pyridine, dimethylformamide, trimethylamine and dimethylaniline [J. Biol. Chem., 239, 2986 (1964)].

The reaction product is collected as a precipitate produced by addition of an organic solvent such as alcohol or acetone to the reaction mixture, or by purification by gel filtration on Sephadex G-25 or by dialysis.

Sulfuric acid ester of β-1,3-glucan in this invention can also be used as the salts thereof, such as salts with basic inorganic substances, including ammonium salts, alkali metal salts (e.g. sodium salts, potassium salts), and alkali earth metal salts (e.g. calcium salts, magnesium salts).

Sulfuric acid ester of β-1,3-glucan, being highly soluble in water, less toxic, and relatively less anticoagulant, can avoid the side effects caused by heparin etc.

Steroidal and non-steroidal substances which are combined with dextran sulfate, β-1,3-glucan sulfate, or a salt thereof to accelerate the angiostatic activity in this invention need not be angiostatic by themselves. Following substances are the examples.

The said steroidal substances include those known also as angiostatic steroids such as cortisone, hydrocortisone, tetrahydrocortisol, hydrocortisone-21-phosphate, 17α-hydroxyprogesterone, 11α-epihydrocortisol, cortexolon, corticosterone, desoxycorticosterone, testosterone, estrone, medroxyprogesterone and dexamethasone (J. Folkman et al.; Science, 221, 719 (1983), J. Folkman et al.; Annals of Surgery, 206, 374 (1987)).

The said non-steroidal substances include collagen synthesis inhibitors, fumagillin, and the derivatives thereof. Collagen synthesis inhibitors include proline analogs and specific inhibitors of collagen proline hydroxylase. It has been reported that proline analogs are incorporated into the collagen molecules instead of proline molecules to form abnormal collagen molecules which are easily degraded, and thus suppress accumulation of collagen. There include, for example, L-azetidine-2-carboxylic acid, cis-hydroxyproline, D,L-3,4-dehydroproline, and thioproline. Some of these proline analogs are weakly angiostatic when used alone, though the angiostatic effect became strong in combination with dextran sulfate, β-1,3-glucan sulfate or a salt thereof.

The specific inhibitors of collagen proline hydroxylase include P-1894 B (H. Okazaki et al.; J. Antibiotics, 34, 1355 (1981), T. Ishimaru et al.; Biochem. Pharmacology, 31, 915 (1982)) and fibrostatins A, B, C, D, E and F (T. Ishimaru et al.; J. Antibiotics, 40, 1231 (1987), K. Ohta et al.; J. Antibiotics, 40, 1239 (1987)), which were isolated as metabolites of microorganisms, shown to inhibit specifically accumulation of collagen, and can be used in this invention.

These specific inhibitors of collagen proline hydroxylase are angiostatic even when used alone, though they exert the angiostatic effect more effectively at a lower concentration when combined with dextran sulfate, β-1,3-glucan sulfate, or a salt thereof.

Derivatives of fumagillin include fumagillol, a hydrolyzate of fumagillin, (Tarbell, D. S. et al., Journal of American Chemical Society, 83, 3096 (1961)) and the related compounds, O-substituted fumagillol derivatives. The O-substituted fumagillol derivatives are the compounds and the salts thereof, represented by the general formula (II):

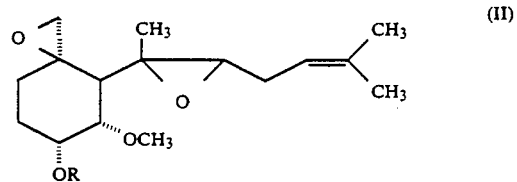

wherein, R represents (1) a substituted alkanoyl group, (2) an aroyl group substituted with an alkyl having 2 to 6 carbon atoms, amino, halogen, hydroxyl, lower alkoxy, cyano, carbamoyl, or carboxyl, (3) an aromatic heterocyclic carbonyl group which may be substituted, (4) a carbamoyl group which may be substituted, (5) an alkyl group which may be substituted, or (6) a benzenesulfonyl or alkylsulfonyl group which may be substituted.

In the general formula shown above, the substituted alkanoyl groups represented by R include alkanoyl groups (desirably having one to twenty carbon atoms; unsubstituted alkanoyl groups are exemplified by formyl, acetyl, propionyl, isopropionyl, butylyl, pentanoyl, hexanoyl, heptanoyl, octanoyl, nonanoyl, lauroyl, undecanoyl, myristoyl, palmitoyl, stearoyl, arachinoyl) substituted with desirably one to three of amino, lower ($C_{1-3}$) alkylamino (e.g. methylamino, ethylamino, isopropylamino), di-lower($C_{1-3}$) alkylamino (e.g. dimethylamino, diethylamino), nitro, halogen (e.g. fluorine, chlorine, bromine, iodine), hydroxyl, lower ($C_{1-3}$) alkoxy (e.g. methoxy, ethoxy), cyano, carbamoyl, carboxyl, lower($C_{1-3}$) alkoxycarbonyl (e.g. methoxycarbonyl, ethoxycarbonyl), carboxy lower($C_{1-3}$) alkoxy (e.g. carboxymethoxy, 2-carboxyethoxy), phenyl which may be substituted, aromatic heterocyclic groups (desirably 5- to 6-membered aromatic heterocyclic groups containing one to four hetero atoms such as nitrogen, oxygen, or sulfur, such as 2-furyl, 2-thienyl, 4-thiazolyl, 4-imdazolyl, and 4-pyridyl). Among them 3-carboxypropionyl and 4-carboxybutylyl are preferable.

The aroyl groups represented by R include benzoyl, 1-naphthoyl, and 2-naphthoyl substituted desirably with one to three of lower alkyl having two to six carbon atoms such as ethyl and propyl, amino, halogen (e.g. fluorine, chlorine, bromine), hydroxyl, lower($C_{1-3}$) alkoxy (e.g. methoxy, ethoxy), cyano, carbamoyl, or carboxyl groups. Among them 2-carboxybenzoyl is preferable.

The substituents in the aromatic heterocyclic carbonyl groups which may be substituted and represented by R include those in the substituted aroyl groups described above. The aromatic heterocyclic carbonyl groups are 5- or 6-membered groups containing one to four heteroatoms each such as nitrogen, oxygen and sulfur, among which 2-furoyl, 2-thenoyl, nicotinoyl and isonicotinoyl are preferable.

The carbamoyl groups which may be substituted and are represented by R include carbamoyl groups, mono-substituted carbamoyl groups and di-substituted carbamoyl groups, and the substituents include lower(-$C_{1-4}$) alkyl (e.g. methyl, ethyl, propyl, butyl), lower alkanoyl (preferably having one to six carbon atoms, e.g. acetyl, propionyl), chloroacetyl, trichloroacetyl, lower($C_{1-3}$) alkoxycarbonylmethyl (e.g. methoxycarbonylmethyl, ethoxycarbonylmethyl), carboxymethyl, phenyl, naphthyl and benzoyl which may be substituted, and those which form ring amino groups (e.g. pyrrolidino, piperidino, morpholino, piperazino, 4-methylpiperazino, 4-phenylpiperazino) together with the nitrogen atom in the carbamoyl groups. Among them chloroacetyl, phenyl, and benzoyl are preferable.

Alkyl groups which may be substituted and are represented by R include straight chain and branched alkyl groups having one to twenty carbon atoms each which may be substituted with one to three substituents similar to those in the alkanoyl groups which may be substituted as described above. The said alkyl groups may be epoxidated at a given position. Among these alkyl groups, methyl, ethyl, and benzyl are preferable.

The substituents in the benzenesulfonyl groups which may be substituted and are represented by R include lower ($C_{1-3}$) alkyl (e.g. methyl, ethyl) and halogen (e.g. fluorine, chlorine, bromine), and one to three of these substituents may be at given positions on the benzene ring.

The alkylsulfonyl groups which may be substituted and are represented by R include lower alkylsulfonyl groups having one to six carbon atoms each which may be substituted with one to three substituents similar to those in the substituted alkanoyl groups described above. Among these groups methylsulfonyl and ethylsulfonyl are preferable.

In the general formula (II) substituents in the phenyl groups which may be substituted include lower($C_{1-4}$) alkyl (e.g. methyl, ethyl, propyl, butyl), lower($C_{1-3}$) alkoxy (e.g. methoxy, ethoxy, propoxy), halogen (e.g. fluorine, chlorine, bromine), halogenated alkyl (e.g. trifluoromethyl, chloromethyl), and nitro, and one to five of these substituents may be at given positions on the phenyl ring.

When the compound represented by the general formula (II) has an acidic substituent (e.g. carboxyl) or a basic substituent (e.g. amino, lower alkylamino, di-lower alkylamino), the pharmaceutically acceptable salts of the compounds may also be used. The pharmaceutically acceptable salts include salts with inorganic bases, salts with organic bases, salts with inorganic acids, salts with organic acids, and salts with basic or acidic amino acids. Inorganic bases to form such salts include alkali metals (e.g. sodium, potassium) and alkali earth metals (e.g. calcium, magnesium); organic bases include trimethylamine, triethylamine, pyridine, picoline, N,N-dibenzylethylenediamine, ethanolamine, diethanolamine, tris(hydroxymethyl)aminomethane and dicyclohexylamine; inorganic acids include hydrochloric acid, hydrobromic acid, sulfuric acid, nitric acid and phosphoric acid; organic acids include formic acid, acetic acid, trifluoroacetic acid, oxalic acid, tartaric acid, fumaric acid, maleic acid, methanesulfonic acid, benzenesulfonic acid and p-toluenesulfonic acid; basic or acidic amino acids include arginine, lysine, ornithine, aspartic acid and glutamic acid. Among these salts, salts with bases (i.e. salts with inorganic bases, salts with organic bases, salts with basic amino acids) mean salts which are formed with the carboxyl group in the substituent of the compound (II), and salts with acids (i.e. salts with inorganic acids, salts with organic acids, salts with acidic amino acids) mean salts which are formed with the amino group, lower alkylamino group, or di-lower alkylamino group in the substituent of the compound (II).

The O-substituted fumagillol derivatives described above are by themselves angiostatic showing low toxicity.

O-Substituted fumagillol derivatives represented by the general formula (II) can be produced by acylation, carbamoylation, alkylation, or sulfonylation of fumagillol with an acylating agent, carbamoylating agent, alkylating agent or sulfonylating agent, respectively, as described below. When the acylating agent, carbamoylating agent, alkylating agent or sulfonylating agent contains as substituent such as amino, hydroxyl or carboxyl, these substituents are preferably protected, and appropriate protective groups are chosen according to the stability of the products. Desirable protective groups include 4-nitrobenzyloxycarbonyl and 2-trimethylsilylethoxycarbonyl for amino group, 4-nitrobenzyl and t-butyldimethylsilyl for hydroxyl group, and 4-nitorbenzyl for carboxyl group. For removal of such protective groups, routine methods such as catalytic reduction and reaction with fluoride ion are employable. For carbamoylation and alkylation, lower alkyl groups such as methyl group and ethyl group are also usable as protecting groups for carboxyl group and can be removed by hydrolysis under mild alkaline condition after reaction.

The acylation described above is performed by allowing fumagillol to react with a reactive derivative of an activated carboxylic acid such as acid anhydride and acid halide (e.g. acid chloride, acid bromide).

The alkylation described above is performed by allowing fumagillol to react with an alkylating agent such as alkyl halide represented by $R^2Y$ [wherein, $R^2$ means (5) alkyl groups which may be substituted as defined above for R, Y means a Leaving group (e.g. halogen (chlorine, bromine, iodine, etc.))] and dialkyl sulfate (e.g. dimethyl sulfate, diethyl sulfate).

Carbamoylation to introduce a mono-substituted carbamoyl group is performed usually by allowing fumagillol to react with isocyanate. For example the following reaction is used.

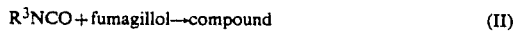

$R^3NCO + \text{fumagillol} \rightarrow \text{compound}$ (II)

wherein $R^3$ represents the substituents for the carbamoyl groups which may be substituted and are represented by R as described above, including lower alkyl, lower alkanoyl, and chloroacetyl.

Sulfonylation is performed by allowing fumagillol to react with an activated sulfonic acid derivative such as sulfonic acid anhydride and sulfonic acid halide (e.g. sulfonyl chloride, sulfonyl bromide).

That is, the reaction is written as follows:

reactive derivative of
R⁴OH + fumagillol→compound    (II)

wherein R⁴ is (6) benzenesulfonyl or alkylsulfonyl group which may be substituted as defined above for R.

The angiostatic agents of this invention are very useful as preventive therapeutics for many diseases caused by abnormally accelerated angiogenesis. Such diseases include, as described above, diabetic retinopathy, retrolenticular fibroplasia, angiogenesis following keratoplasty, glaucoma, ocular tumor and trachoma in ophthalmology, psoriasis and purulent granuloma in dermatology, hemangioma and fibrous hemangioma in pediatrics, hypertrophic scar and granulation in surgery, rheumatic arthritis and edematous sclerosis in internal medicine, and arteriosclerosis and various tumors among heart diseases.

The preparations of this invention are administered orally or parenterally to mammals (e.g. rat, rabbit, monkey, human) in the form of tablet, granule, capsule, syrup, powder, injection, cream for local application, or eye drop. Pharmaceutical compositions used together with the active substance for production of the preparations of various drug forms may contain appropriate additives (raw materials for preparations) such as excipients, binders, disintegrators, lubricants, coloring agents, flavoring agents, and stabilizers. The preparations may be administered after processing into sustained release preparations using sustained release polymers etc. For example, the preparations are incorporated in pellets of ethylenevinylacetate polymer which are then implanted surgically into the tissues to be treated.

For example for treatment of diabetic retinopathy, compositions containing a pharmaceutically acceptable carrier are given orally or by intravenous injection. For treatment of the retinopathy or trachoma, the compositions are given also in the form of eye drops once to four times a day according to the state of the patient.

The dosis may be any effective dose determined according to the patient and the pathological state to be treated and administration route. For example dextran sodium sulfate or β-1,3-glucan sodium sulfate is usually given orally or parenterally in 1 to 3 daily doses of 10 mg to 900 mg.

When a steroid or a non-steroidal substance described above is to be combined, about 0.005 to 50 weight parts of the steroid or about 0.005 to 300 weight parts of the non-steroidal substance is generally used for one weight part of dextran sulfate, β-1,3-glucan sulfate, or a salt thereof, though the rate varies according to the angiostatic activity of the substance used.

In this invention (a) dextran sulfate, β-1,3-glucan sulfate, or a salt thereof, and (b) a steroid or a non-steroidal substance described above may be used as a preparation containing both (a) and (b) or in combination of a preparation containing (a) and a preparation containing (b); that is they are given so that the combined effect may be induced in the body.

EXAMPLES

The following reference examples, test examples, and examples will illustrate this invention in detail.

REFERENCE EXAMPLE 1

2.5 g of β-1,3-glucan (curdlan) with the mean degree of polymerization of 540 was suspended in 100 ml of dimethylformamide, to which 12.5 g of triethylaminesulfonic acid synthesized from 13.5 g of chlorosulfonic acid and 11.7 g of triethylamine was added and allowed to react in ice water for 24 hours by stirring. The reaction mixture was dialyzed thoroughly against 0.5M sodium carbonate and freeze-dried, to give 4.6 g of the desired substance. The mean degree of substitution ($\overline{DS}$) of β-1,3-glucan sodium sulfate thus obtained was 1.04 (sulfur content: 12.7%). In the following test examples and examples this preparation of β-1,3-glucan sodium sulfate was used.

REFERENCE EXAMPLES 2

O-Chloroacetylcarbamoyl fumagillol

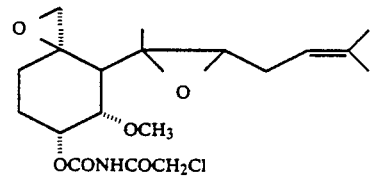

To a solution of fumagillol (314 mg) in dichloromethane (5 ml), chloroacetyl isocyanate (160 mg) was added dropwise with ice-cooling, followed by addition of dimethylaminopyridine (130 mg) and stirring at 0° C. for 2 hours. The reaction mixture was treated with water and extracted with dichloromethane. The organic layer was washed with saturated saline and dried with anhydrous magnesium sulfate. The solvent was evaporated under reduced pressure, and the residue was subjected to silica gel column chromatography. The eluate with n-hexane-ethyl acetate (3:1) was concentrated under reduced pressure, to give 318 mg (yield: 71%) of O-chloroacetylcarbamoyl fumagillol as a colorless powder.

¹H-NMR(CDCl₃)δ:
1.10(1H,m),1.21(3H,s),1.66(3H,s),1.75(3H,s),1.93(1H,d,-J=11.4 Hz),1.8–2.5(5H,m),2.57(1H,d,J=4.2 Hz),2.58(1H,m),2.99(1H,d,J=4.2 Hz),3.47(3H,s),3.68(1H,dd,J=11.4 Hz,J=2.8 Hz),4.44(2H,s),5.20(1H,m),5.61(1H,m),8.33(1H,brs).

Measurement of Angoistatic Activity

Angiostatic activity was measured by the shell-less chorioallantoic membrane (CAM) assay, reported by J. Folkman et al. (R. Crum et al.; Science, 230, 1375 (1985)) with slight modifications. That is, a chick embryo obtained by breaking the shell of a chick fertilized egg which had been cultivated for three days was hung like a hammock with poly(vinylidene dichloride) in a plastic cup and subjected to sterile culture for further 5 days.

The test sample was prepared as follows: Dextran sodium sulfate or β-1,3-glucan sodium sulfate, alone or in combination with a steroid or a non-steroidal substance described above, was dissolved in aqueous methylcellulose solution (final concentration 0.5%) ten microliter of the resultant solution was quietly placed dropwise on a Teflon plate, and air-dried under sterile condition, to give a methylcellulose disk of about 4 mm in diameter containing the sample. The methylcellulose disk, prepared as described above, was placed gently onto a chorioallantoic membrane, which had been cultured for 5 days after shell-breaking. The culture of the embryo was then continued under sterile condition. Twenty-four or 48 hours later, the avascular zone formed around the disk was examined microscopically (×20, SMZ-10, Nikon). Angiostatic activity (%) was determined by counting the disks which showed an avascular zone.

TEST EXAMPLE 1

Angiostatic activity of dextran sodium sulfate (mean molecular weight: 500,000, manufactured by Sigma Co.) and β-1,3-glucan sodium sulfate was measured, and the results are summarized in Table 1.

TABLE 1

|  | Sample amount μg/disk | Angiostatic activity* (%) |
|---|---|---|
| dextran | 50 | 100 |
| sodium sulfate | 12.5 | 89 |
|  | 3.1 | 83 |
| β-1,3-glucan | 50 | 89 |
| sodium sulfate | 12.5 | 83 |

*measured after 48 hours

TEST EXAMPLE 2

Dextran sodium sulfate (mean molecular weight: 500,000, manufactured by Sigma Co.) or β-1,3-glucan sodium sulfate combined with hydrocortisone (manufactured by Sigma Co.) was tested, and the results showed that the angiostatic effect is increased or potentiated by combination (Table 2).

TABLE 2

|  | Sample amount μg/disk | Angiostatic activity* (%) |
|---|---|---|
| dextran sodium sulfate | hydrocortisone |  |
| 1.3 | 0 | 39 |
| 1.3 | 0.4 | 33 |
| 1.3 | 2 | 44 |
| 1.3 | 10 | 78 |
| β-1,3-glucan sodium sulfate | hydrocortisone |  |
| 5.1 | 0 | 33 |
| 5.1 | 2 | 44 |
| 5.1 | 10 | 67 |

*measured after 24 hours

TEST EXAMPLE 3

Dextran sodium sulfate (mean molecular weight: 500,000, manufactured by Sigma Co.) or β-1,3-glucan sodium sulfate combined with fumagillin or the compound in Reference Example 2 was tested, and the results showed that the angiostatic effect is potentiated by combination as shown in Table 3.

TABLE 3

|  | Sample amount μg/disk | Angiostatic activity* (%) |
|---|---|---|
| fumagillin | 30 | 44 |
| fumagillin | 100 | 89 |
| the compound of Reference Example (2) | 10 | 0 |
| the compound of Reference Example (2) | 30 | 44 |
| dextran sodium sulfate 1.3 + fumagillin + | 30 | 39 63 |
| the compound of Reference Example (2) | 10 | 67 |
| β-1,3-glucan sodium sulfate 5.1 + | 30 | 33 88 |

TABLE 3-continued

|  | Sample amount μg/disk | Angiostatic activity* (%) |
|---|---|---|
| fumagillin + the compound of Reference Example (2) | 10 | 63 |

*measured after 24 hours

TEST EXAMPLE 4

Dextran sodium sulfate (mean molecular weight: 500,000, manufactured by Sigma Co.) or β-1,3-glucan sodium sulfate combined with a collagen synthesis-inhibiting proline analog, P-1894B (a specific inhibitor of collagen proline hydroxylase), or fibrostatin C was tested for angiostatic activity. As can be seen from Table 4, the results showed that each of these compounds is angiostatic and combination with dextran sodium sulfate or β-1,3-glucan sodium sulfate potentiates the angiostatic effect.

TABLE 4

|  | Sample amount μg/disk | Angiostatic activity* (%) |
|---|---|---|
| azetidine-2-carboxylic acid | 100 | 22 |
| azetidine-2-carboxylic acid | 300 | 38 |
| cis-hydroxyproline | 300 | 33 |
| P-1894B | 1 | 44 |
| P-1894B | 3 | 83 |
| fibrostatin C | 60 | 20 |
| fibrostatin C | 100 | 67 |
| dextran sodium sulfate 1.3 + azetidine-2-carboxylic acid + | 100 | 39 44 |
| cis-hydroxyproline + | 300 | 58 |
| P-1894B + | 1 | 56 |
| fibrostatin C | 60 | 60 |
| β-1,3-glucan sodium sulfate 5.1 + azetidine-2-carboxylic acid + | 100 | 33 78 |
| cis-hydroxyproline + | 300 | 56 |
| P-1894B + | 1 | 78 |
| fibrostatin C | 60 | 67 |

*measured after 24 hours

EXAMPLE 1

Capsules

| (1) dextran sodium sulfate | 100 mg |
|---|---|
| (mean molecular weight 500,000, S content 16.8%) | |
| (2) lactose | 135 mg |
| (3) corn starch | 60 mg |
| (4) magnesium stearate | 5 mg |
| one capsule contains | 300 mg |

Ingredients (1), (2), and (3) and a half the amount of (4) are mixed and granulated by a conventional method. The remainder of the ingredient (4) is added and included into No. 1 gelatin capsules (Japanese Pharmacopoeia X) by a conventional method, to make capsules.

EXAMPLE 2

Capsules

| (1) β-1,3-glucan sodium sulfate | 100 mg |
|---|---|
| (2) lactose | 135 mg |
| (3) corn starch | 60 mg |
| (4) magnesium stearate | 5 mg |
| one capsule contains | 300 mg |

Ingredients (1), (2), and (3) and a half the amount of (4) are mixed and granulated by a conventional method.

The remainder of the ingredient (4) is added and included into No. 1 gelatin capsules (Japanese Pharmacopoeia X) by a conventional method, to make capsules.

EXAMPLE 3

Capsules

| | |
|---|---|
| (1) fibrostatin | 100 mg |
| (2) β-1,3-glucan sodium sulfate | 50 mg |
| (3) lactose | 135 mg |
| (4) corn starch | 60 mg |
| (5) magnesium stearate | 5 mg |
| one capsule contains | 350 mg |

Ingredients (1), (2), (3), and (4) and a half the amount of (5) were mixed and granulated by a conventional method. The remainder of the ingredient (5) was added and included into No. 1 gelatin capsules (Japanese Pharmacopoeia X) by a conventional method, to make capsules.

EXAMPLE 4

Eye Drop

| | |
|---|---|
| hydrocortisone | 0.2 g |
| dextran sodium sulfate | 0.5 g |
| (mean molecular weight: 5,000, S content 17.2%) | |
| boric acid | 16 g |
| sodium borate | 7 g |
| methyl p-hydroxybenzoate | 0.25 g |
| propionyl p-hydroxybenzoate | 0.15 g |

To the mixture of these ingredients sterile distilled water is added to make 1 l. The solution obtained by filtration and sterilization is used as eye drop.

EXAMPLE 5

Eye Drop

| | |
|---|---|
| sodium salt of fumagillin | 5 g |
| dextran sodium sulfate | 1 g |
| (mean molecular weight: 5,000, S content 17.2%) | |
| methyl p-hydroxybenzoate | 0.25 g |
| propionyl p-hydroxybenzoate | 0.15 g |
| dibasic sodium phosphate | 4.0 g |
| sodium chloride | 8.4 g |

To the mixture of these ingredients sterile distilled water is added to make 1 l. The pH is adjusted to 7.5 and the solution obtained by filtration and sterilization is used as eye drop.

EXAMPLE 6

Eye Drop

| | |
|---|---|
| P-1894B | 0.1 g |
| β-1,3-glucan sodium sulfate | 0.5 g |
| methyl p-hydroxybenzoate | 0.25 g |
| propionyl p-hydroxybenzoate | 0.15 g |
| dibasic sodium phosphate | 4.0 g |
| sodium chloride | 8.5 g |

To the mixture of these ingredients sterile distilled water is added to make 1 l. The pH is adjusted to 7.5 and the solution obtained by filtration and sterilization is used as eye drop.

What is claimed is:

1. A method for prophylaxis or treatment of a disease caused by abnormally accelerated angiogenesis in a mammal, which comprises administering an angiostatic agent comprising dextran sulfate, β-1,3-glucansulfate, or a pharmaceutically acceptable salt thereof in combination with pharmaceutically acceptable carrier to the mammal.

2. The method according to claim 1, wherein the dextran sulfate has a mean molecular weight between about 5,000 to about 500,000 and a degree of sulfation in the dextran sulfate of about 16 to 18 weight % in terms of sulfur content.

3. The method according to claim 1, wherein the angiostatic agent is further used together with a steroidal substance which is a member selected from the group consisting of cortisone, hydrocortisone, tetrahydrocortisol, hydrocortisone-21-phosphate, 17α-hydroxyprogesterone, 11α-epihydrocortisol, cortexolon, corticosterone, desoxycorticosterone, testosterone, estrone, medroxyprogesterone and dexamethasone, or with a non-steroidal substance which is a member selected from the group consisting of a collagen synthesis inhibitor, fumagillin and fumagillin derivative, which accelerates the angiostatic activity.

4. The method according to claim 3, wherein the collagen synthesis inhibitor is a proline analog selected from the group consisting of L-azetidine-2-carboxylic acid, cis-hydroxyproline, D,L-3,4-dehydroproline and thioproline.

5. The method according to claim 3, wherein the collagen synthesis inhibitor is a specific inhibitor of collagen proline hydroxylase selected from the group consisting of P-1894B, and fibrostatin, A, B, C, D, E and F.

6. The method according to claim 1, wherein the amount of said agent administered to the mammal is 10 mg. to 900 mg. per day.

7. The method according to claim 1, wherein the β-1,3-glucan sulfate is of the formula:

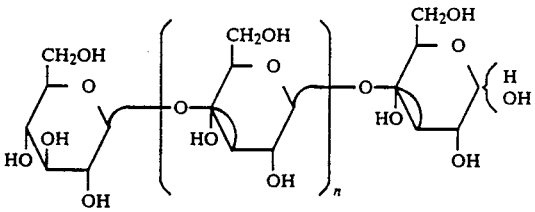

wherein n is an integer from 4 to about 1,000 and appropriate number of three hydroxyl groups of the intermediate monosaccharide units and the hydroxyl groups of the terminal monosaccharide units are sulfated.

8. The method according to claim 7, wherein the mean degree of polymerization of the β-1,3-glucan sulfate is less than 1,000 and the mean degree of substitution of the β-1,3-glucan sulfate is 0.5 to 3 per monosaccharide.

* * * * *